(12) United States Patent
Corma

(10) Patent No.: US 7,615,667 B2
(45) Date of Patent: Nov. 10, 2009

(54) PROCESS FOR PRODUCING CYCLOALKANOL AND/OR CYCLOALKANONE

(75) Inventor: Avelino Corma, Valencia (ES)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/269,154

(22) Filed: Nov. 12, 2008

(65) Prior Publication Data

US 2009/0131724 A1 May 21, 2009

(30) Foreign Application Priority Data

Nov. 21, 2007 (JP) ............................. 2007-301353

(51) Int. Cl.
*C07C 45/33* (2006.01)
*C07C 35/08* (2006.01)

(52) U.S. Cl. .................. 568/360; 568/835; 568/836

(58) Field of Classification Search .............. 568/360, 568/835, 836

See application file for complete search history.

(56) References Cited

U.S. PATENT DOCUMENTS

| 6,160,183 | A | 12/2000 | Druliner et al. |
| 2006/0224020 | A1 | 10/2006 | Corma et al. |

FOREIGN PATENT DOCUMENTS

| JP | 10-505867 A | 6/1998 |
| JP | 2006-273780 A | 10/2006 |

OTHER PUBLICATIONS

S. Liu et al., "Liquid-Phase Oxidation of Cyclohexane Using Co-P-MCM-41 Catalyst", Korean J. Chem. Eng. 15(5), 1998, pp. 510-515.
G. Lu et al., "Gold nanoparticles in mesoporous materials showing catalytic selective oxidation cyclhexane using oxygen", Applied Catalysis A, General 280, (2000), pp. 175-180.
S. Shylesh et al., "Chromium-containing small pore mesoporous silicas: Synthesis, characterization and catalytic behavior in the liquid phase oxidation of cyclohexane", Applied Catalysis A: General 318, (2007), pp. 128-136.
G. Qian et al., "Oxidation of Cyclohexane over Bi-incorporated MCM-41 Mesoporous Molecular Sieve Catalyst with Oxygen as Oxidant", Chemistry Letters vol. 34, No. 2, (2005), pp. 162-163.

*Primary Examiner*—Sikarl A Witherspoon
(74) *Attorney, Agent, or Firm*—Sughrue Mion, PLLC

(57) ABSTRACT

An object of the present invention is to provide a process capable of producing cycloalkanol and/or cycloalkanone with a favorable selectivity by oxidizing cycloalkane with a favorable conversion.

Cycloalkanol and/or cycloalkanone are produced by oxidizing cycloalkane with oxygen in the presence of a catalyst comprising calcium oxide and a transition metal supported on the calcium oxide. The transition metal is preferably at least one metal selected from cobalt, gold, vanadium, chromium, manganese, iron, ruthenium and palladium, and more preferably cobalt or gold.

4 Claims, No Drawings

PROCESS FOR PRODUCING CYCLOALKANOL AND/OR CYCLOALKANONE

BACKGROUND OF THE INVENTION

1. Field of the Invention

This application claims priority under the Paris Convention on Japanese Patent Application No. 2007-301353 filed on Nov. 21, 2007, the entire content of which is herein incorporated by reference.

The present invention relates to a process for producing cycloalkanol and/or cycloalkanone by oxidizing cycloalkane with oxygen.

2. Description of the Related Art

As the process for producing cycloalkanol and/or cycloalkanone by oxidizing cycloalkane with oxygen, for example, a process for performing the oxidation reaction in the presence of a catalyst wherein a transition metal such as cobalt, gold, chromium or the like is supported on silica, alumina, zirconia, carbon or titania (cf. U.S. Pat. No. 6,160,183), a process for performing the oxidation reaction in the presence of a catalyst wherein manganese is supported on metallosilicate or aluminophosphate (cf. Published Japanese Translation No. 10-505867 of the PCT Application), a process for performing the oxidation reaction in the presence of a catalyst wherein gold is supported on cerium oxide, and a process for performing the oxidation reaction in the presence of a catalyst wherein a transition metal such as cobalt, gold, chromium, bismuth or the like is supported on mesoporous silica (for example, refer to Korean Journal of Chemical Engineering, (Republic of Korea), 1998, Vol. 15, pp. 510-515; Applied Catalysis A: General, (Netherlands), 2005, Vo. 280, pp. 175-180; Applied Catalysis A: General, (Netherlands), 2007, Vo. 318, pp. 128-136; and Chemistry Letters, (Japan), 2005, Vol. 34, pp. 162-163).

SUMMARY OF THE INVENTION

The above-mentioned conventional process sometimes includes unsatisfactory points in view of activity and selectivity of a catalyst, namely, the conversion of cycloalkane and the selectivity of cycloalkanol and/or cycloalkanone. Thus, an object of the present invention is to provide a process capable of producing cycloalkanol and/or cycloalkanone with a favorable selectivity by oxidizing cycloalkane with a favorable conversion.

The present inventors have intensively studied and found that the above object can be achieved by performing the above oxidation reaction in the presence of a catalyst comprising calcium oxide and a transition metal supported on the calcium oxide. Thus, the present invention has been completed.

That is, the present invention provides a process for producing cycloalkanol and/or cycloalkanone, which comprises oxidizing cycloalkane with oxygen in the presence of a catalyst comprising calcium oxide and a transition metal supported on the calcium oxide.

According to the present invention, cycloalkanol and/or cycloalkanone can be produced with a favorable selectivity by oxidizing cycloalkane with a favorable conversion.

DETAILED DESCRIPTION OF THE INVENTION

The present invention will now be described in detail. In the present invention, the corresponding cycloalkanol and/or cycloalkanone is/are produced by oxidizing cycloalkane used as a starting material with oxygen (molecular oxygen) in the presence of a predetermined catalyst.

Examples of the cycloalkane as the raw material include monocyclic cycloalkanes having no substituent on the ring, such as cyclopropane, cyclobutane, cyclopentane, cyclohexane, cycloheptane, cyclooctane, cyclodecane, and cyclooctadecane; polycyclic cycloalkanes such as decalin and adamantane; and cycloalkanes having a substituent on the ring, such as methylcyclopentane and methylcyclohexane, and also two or more kinds of them can be used, if necessary.

An oxygen-containing gas is usually used as the oxygen source. This oxygen-containing gas may be, for example, air, pure oxygen, or an air or pure oxygen diluted with an inert gas such as nitrogen, argon or helium. Oxygen enriched air obtained by adding pure oxygen to air can also be used.

In the present invention, the above oxidation reaction is conducted in the presence of a catalyst comprising calcium oxide and a transition metal supported on the calcium oxide (hereinafter occasionally referred to as a transition metal-supporting catalyst). Using such a catalyst, cycloalkanol and/or cycloalkanone can be produced with a favorable selectivity by oxidizing cycloalkane with a favorable conversion.

Examples of the transition metal include metals having catalytic activity to the above oxidation reaction. Among these transition metals, cobalt, gold, vanadium, chromium, manganese, iron, ruthenium and palladium are preferable. If necessary, two or more kinds of these transition metals may be used. Among these transition metals, cobalt and gold are more preferable, and cobalt is still more preferable.

The content of the transition metal is usually from 0.01 to 20%, preferably from 0.05 to 10%, and still more preferably from 0.1 to 5%, in terms of a weight ratio of the metal to the transition metal-supporting catalyst.

Examples of the process of supporting the transition metal on calcium oxide include a process of impregnating calcium oxide with a solution of a metal compound such as a halogenate, a nitrate, a sulfate, a carboxylate, an oxo-acid salt or a hydroxide of the metal; and a process of immersing calcium oxide in a solution of the metal compound thereby adsorbing the metal compound to the calcium oxide. The amount of the metal compound used is appropriately adjusted so as to control to the content of the metal.

It is possible to use, as the raw material of the transition metal, cobalt compounds such as cobalt bromide, cobalt chloride, cobalt fluoride, cobalt nitrate, cobalt sulfate, cobalt acetate, cobalt naphthate, and cobalt hydroxide; gold compounds such as gold chloride, tetrachloroauric(III) acid and gold hydroxide; vanadium compounds such as vanadium bromide, vanadium chloride, vanadium fluoride, and vanadium naphthate; chromium compounds such as chromium chloride, chromium nitrate, chromium sulfate, chromium acetate, and chromium naphthate; manganese compounds such as manganese bromide, manganese chloride, manganese fluoride, manganese nitrate, manganese ammonium sulfate, manganese sulfate, manganese acetate, and manganese naphthate; iron compounds such as iron bromide, iron chloride, iron fluoride, iron nitrate, iron sulfate, iron acetate, and iron naphthate; ruthenium compounds such as ruthenium bromide and ruthenium chloride; and palladium compounds such as palladium bromide, palladium chloride, palladium nitrate, palladium sulfate, and palladium hydroxide. Among these compounds, cobalt compounds and gold compounds are preferable, and cobalt compound are more preferable.

Calcium oxide as the carrier to be used may be commercially available calcium oxide, and can be prepared by calcining calcium hydroxide.

As described above, the transition metal is supported on calcium hydroxide and is usually dried. It is more effective to further calcine after drying.

The above calcination reaction can be conducted under an atmosphere of air, nitrogen, hydrogen, helium or the like, and is preferably conducted under an atmosphere of air. The calcination temperature is usually from 200 to 1,000° C., and preferably from 300 to 600° C. The calcination time is from 1 to 40 hours, preferably from 3 to 20 hours, and still more preferably from 5 to 15 hours.

The oxidation reaction of cycloalkane can be conducted by bringing cycloalkane into contact with oxygen in the presence of a transition metal-supporting catalyst. The amount of the catalyst to be used is usually from 0.01 to 50 parts by weight, and preferably from 0.1 to 10 parts by weight, based on 100 parts by weight of cycloalkane.

The reaction temperature is usually from 0 to 200° C., and preferably from 50 to 170° C., and the reaction pressure is usually from 0.01 to 10 MPa, and preferably from 0.1 to 2 MPa. The reaction solvent can be used, if necessary, and it is possible to use nitrile solvents such as acetonitrile and benzonitrile, and carboxylic acid solvents such as acetic acid and propionic acid.

The above oxidation reaction can also be used in the presence of a radical polymerization initiator, in addition to the transition metal-supporting catalyst. Examples of the radical initiator include azonitrile compounds such as 2,2'-azobis(isobutyronitrile), 2,2'-azobis(2,4-dimethylvaleronitrile), and 2,2'-azobis(4-methoxy-2,4-dimethylvaleronitrile); and peroxides such as peroxydibenzoyl, peroxydilauroyl, t-butylperoxy-2-ethylhexanoate, and bis(2-ethylhexyl)peroxydicarbonate. Two or more kinds of these radical initiators may be used in combination. Among these radical initiators, azonitrile compounds are preferable, and 2,2'-azobis(isobutyronitrile) is particularly preferable. When the radical initiator is used, the amount is usually from 0.1 mol or less per mol of cycloalkane.

A post-treatment after the oxidation reaction is not specifically limited and examples thereof include a process of filtering the reaction mixture thereby separating the catalyst, followed by washing with water and further distillation. When cycloalkyl hydroperoxide corresponding to the cycloalkane as the starting material is contained in the reaction mixture, it can be converted into the objective cycloalkanol and cycloalkanone by alkali treatment or reduction treatment.

EXAMPLES

Hereinafter, the present invention is described by way of Examples, but the present invention is not limited thereto. Cyclohexane, cyclohexanone, cyclohexanol and cyclohexyl hydroperoxide in the reaction solution were analyzed by gas chromatography, and the conversion of cyclohexane as well as each selectivity of cyclohexanone, cyclohexanol and cyclohexyl hydroperoxide was calculated from the analysis results.

Reference Example 1

Preparation of Cobalt-Supporting Calcium Oxide

Calcium hydroxide was calcined under an air atmosphere at 300° C. for 15 hours to obtain calcium oxide. This calcium oxide was added to 2.84 g of an aqueous solution containing 0.337 g of cobalt(II) acetate tetrahydrate, followed by stirring at room temperature. The resultant solid was filtered and then dried at 150° C. for 15 hours. The solid was washed with water, filtered and then dried at 150° C. for 3 hours. The resultant solid was calcined under an air atmosphere at 400° C. for 8 hours to obtain a cobalt-supporting calcium oxide (cobalt content: 3.4% by weight).

Reference Example 2

Preparation of Gold-Supporting Calcium Oxide

Calcium hydroxide was calcined under an air atmosphere at 300° C. for 15 hours to obtain calcium oxide. 2 g of this calcium oxide was added to 30 ml of water to obtain a suspension A. To an aqueous solution containing 0.178 g of tetrachloroauric(III) acid, 0.2 mol/l of an aqueous sodium hydroxide solution was added thereby adjusting the pH to 10, followed by stirring at room temperature for 18 hours. The resultant solid was filtered, washed with water and then dried at 200° C. for 16 hours to obtain a gold-supporting calcium oxide (gold content: 2% by weight).

Reference Example 3

Preparation of Cobalt-Supporting Kenyaite

In a beaker, 1.13 g of an aqueous solution containing 0.13 g of sodium hydroxide, 1.17 g of tyramine and 2.5 g of colloidal silica (LUDOX AS-40 manufactured by Aldrich Co.; an aqueous suspension of 40 wt % silica) were placed and stirred and an aqueous solution containing 0.14 g of cobalt(II) acetate tetrahydrate was added, followed by stirring for 4 hours. This mixture was transferred to an autoclave, stirred at 150° C. for 10 days and then filtered. The residue was washed with water and then dried at 100° C. for one day to obtain a cobalt-supporting kenyaite.

Example 1

In a 50 ml autoclave, 3.4 g (0.04 mol) of cyclohexane and 0.02 g of the cobalt-supporting calcium oxide obtained in Reference Example 1 were placed. After increasing the pressure in the system to 0.5 MPa at room temperature using oxygen and heating to 130° C., the reaction was carried out under the flow of an oxygen gas for 8 hours.

Three hours after the beginning of the reaction, the conversion of cyclohexane was 5.2%, the selectivity of cyclohexanone was 44.0%, the selectivity of cyclohexanol was 44.3%, and the selectivity of cyclohexyl hydroperoxide was 11.3% (total selectivity: 99.6%). Eight hours after the beginning of the reaction, the conversion of cyclohexane was 7.6%, the selectivity of cyclohexanone was 56.8%, the selectivity of cyclohexanol was 39.5%, and the selectivity of cyclohexyl hydroperoxide was 2.2% (total selectivity: 98.5%). Example 2

In a 50 ml autoclave, 3.4 g (0.04 mol) of cyclohexane, 0.02 g of the gold-supporting calcium oxide obtained in Reference Example 2 and 0.002 g of 2,2'-azobis(isobutylonitrile) were placed. After increasing the pressure in the system to 0.5 MPa at room temperature using oxygen and heating to 130° C., the reaction was carried out under the flow of an oxygen gas for 8 hours.

Three hours after the beginning of the reaction, the conversion of cyclohexane was 2.9%, the selectivity of cyclohexanone was 18.2%, the selectivity of cyclohexanol was 18.0%, and the selectivity of cyclohexyl hydroperoxide was 62.9% (total selectivity: 99.1%). Eight hours after the beginning of the reaction, the conversion of cyclohexane was 6.5%, the selectivity of cyclohexanone was 46.9%, the selectivity of cyclohexanol was 43.3%, and the selectivity of cyclohexyl hydroperoxide was 7.5% (total selectivity: 97.7%).

Comparative Example 1

In a 50 ml autoclave, 3.4 g (0.04 mol) of cyclohexane and 0.02 g of the cobalt-supporting kenyaite obtained in Reference Example 3 were placed. After increasing the pressure in the system to 0.5 MPa at room temperature using oxygen and heating to 130° C., the reaction was carried out under the flow of an oxygen gas for 24 hours.

Three hours after the beginning of the reaction, the conversion of cyclohexane was 1.7%, the selectivity of cyclohexanone was 38.6%, the selectivity of cyclohexanol was 54.2%, and the selectivity of cyclohexyl hydroperoxide was 6.8% (total selectivity: 99.6%). Eight hours after the beginning of the reaction, the conversion of cyclohexane was 4.8%, the selectivity of cyclohexanone was 47.0%, the selectivity of cyclohexanol was 41.3%, and the selectivity of cyclohexyl hydroperoxide was 4.0% (total selectivity: 92.3%). Twenty four hours after the beginning of the reaction), the conversion of cyclohexane was 5.0%, the selectivity of cyclohexanone was 53.6%, the selectivity of cyclohexanol was 20.7%, and the selectivity of cyclohexyl hydroperoxide was 11.5% (total selectivity: 85.8%).

What is claimed is:

1. A process for producing cycloalkanol and/or cycloalkanone, which comprises oxidizing cycloalkane with oxygen in the presence of a catalyst comprising calcium oxide and a transition metal supported on the calcium oxide.

2. The process according to claim 1, wherein the transition metal is at least one metal selected from cobalt, gold, vanadium, chromium, manganese, iron, ruthenium and palladium.

3. The process according to claim 1, wherein the transition metal is cobalt and/or gold.

4. The process according to any one of claims 1 to 3, wherein the cycloalkane is cyclohexane.

* * * * *